United States Patent
Jackson

[11] Patent Number: 6,103,194
[45] Date of Patent: Aug. 15, 2000

[54] APPARATUS FOR TESTING ITEMS OF METAL SUCH AS JEWELRY

[76] Inventor: Richard Jackson, Bassetts Farm, Kippings Cross, Matfield Kent TN12 7HE, United Kingdom

[21] Appl. No.: 09/043,042
[22] PCT Filed: Sep. 12, 1996
[86] PCT No.: PCT/GB96/02249
§ 371 Date: Mar. 10, 1998
§ 102(e) Date: Mar. 10, 1998
[87] PCT Pub. No.: WO97/10500
PCT Pub. Date: Mar. 20, 1997

[30]  Foreign Application Priority Data

Sep. 12, 1995 [GB] United Kingdom ................... 9518563

[51] Int. Cl.[7] ........................ G01N 33/20; G01N 31/22
[52] U.S. Cl. ............................... 422/61; 422/58; 356/30; 436/6; 436/76; 436/80
[58] Field of Search ................ 422/58, 61, 100, 422/101; 356/30; 436/76, 80, 6

[56]  References Cited

U.S. PATENT DOCUMENTS

| | | |
|---|---|---|
| 2,637,244 | 5/1953 | McLeod . |
| 3,446,596 | 5/1969 | Salivar et al. . |
| 4,160,804 | 7/1979 | Victory . |
| 4,635,488 | 1/1987 | Kremer ................................ 422/58 X |
| 4,799,999 | 1/1989 | Medvinsky et al. . |
| 5,171,692 | 12/1992 | Craig, Jr. . |
| 5,278,075 | 1/1994 | Stone ................................... 436/80 X |

FOREIGN PATENT DOCUMENTS

| | | |
|---|---|---|
| 273548 | 7/1988 | European Pat. Off. . |
| 48-55793 | 8/1973 | Japan ..................................... 436/80 |
| 56-92974 | 7/1981 | Japan . |
| 56-98268 | 8/1981 | Japan . |
| 54907 | 6/1982 | Japan . |
| 941439 | 11/1963 | United Kingdom . |
| 1061218 | 3/1967 | United Kingdom . |
| 1067800 | 5/1967 | United Kingdom . |
| 1317312 | 5/1973 | United Kingdom . |
| 2124367 | 2/1984 | United Kingdom . |
| 9307479 | 4/1993 | WIPO . |

*Primary Examiner*—Arlen Soderquist
*Attorney, Agent, or Firm*—Dowell & Dowell, P.C.

[57]  ABSTRACT

Apparatus (1) for testing items of metal such as jewelry comprises a housing (3) which is closed at one end (3a) and partly open at the other end (3b). Sealed within the housing is an insert comprising a reservoir (5) containing a testing chemical and an applicator (7). The applicator extends into the reservoir (5) and projects from the housing through its partly open end (3b). The outer surface of the applicator (7) projecting from the housing forms a tip which is used to apply the testing chemical to the surface of the metal under test.

16 Claims, 1 Drawing Sheet

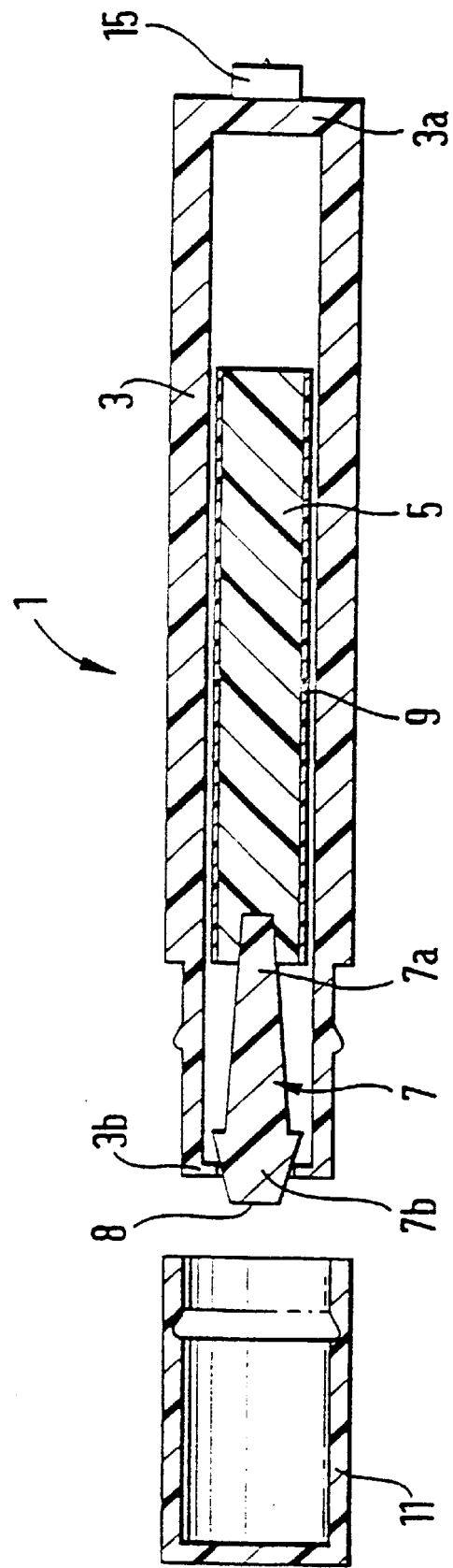

APPARATUS FOR TESTING ITEMS OF METAL SUCH AS JEWELRY

BACKGROUND OF THE INVENTION

1. Field of the Invention

The present invention relates to apparatus for testing items of metal such as jewellery.

2. Brief Discussion of the Related Art

It is known to test items of jewellery or the like with chemicals to determine whether or not they are made of a precious metal or metal alloy and, if so, the grade of such metal. Such chemicals are provided in an "acid set" comprising a set of glass bottles containing different testing chemicals, each bottle having a glass rod or spatula for applying the chemical to the item to be tested. By observing the reaction (or lack of reaction) of the item under test with one or more of the testing chemicals, it is possible to determine whether or not the item contains or comprises metals such as gold, silver, platinum, palladium, copper, or certain other base metals or their alloys.

GB-A-2 124 367 discloses such a known method of testing precious metals.

SUMMARY OF THE INVENTION

The present invention provides apparatus for testing items of metal comprising a reservoir for testing chemical, an applicator for transferring testing chemical from the reservoir to an applying surface thereof and a housing surrounding the reservoir and applicator with the applying surface projecting therefrom. The apparatus is characterised in that the reservoir comprises an absorbent material and the applicator comprises a nib having a wick in contact with testing chemical within the reservoir, and a tip which forms the applying surface.

Preferably the absorbent material of the reservoir is a porous plastic material, such as a fibrous or granular plastics material, preferably comprising polypropylene fibres. The reservoir may be sealed within a film or tube which is resistant to the testing chemical. The nib may comprise any suitable material which will not be deteriorated by the testing chemical. Very preferably the nib is formed of a granular or fibrous plastics material.

The testing chemical may contain one or more of sulphuric acid, nitric acid or hydrochloric acid solution. In addition, the chemical may also contain a small quantity of a silver salt such as silver sulphate or a small quantity of a chromate or dichromate such as sodium chromate.

BRIEF DESCRIPTION OF THE DRAWINGS

The present invention will now be described, by way of example, with reference to the accompanying drawing which is a longitudinal cross-section of an apparatus forming an embodiment of the present invention.

DESCRIPTION OF THE PREFERRED EMBODIMENT

The apparatus 1 comprises a generally cylindrical plastics housing 3. The housing 3 is closed at one end 3a and partly open at the other end 3b. Sealed within the housing is an insert comprising a reservoir 5 containing a testing chemical and an applicator 7.

The reservoir 5 is a cut or moulded cylinder of uniform fibrous, granular or other porous plastic material such as polypropylene which can absorb and retain a testing chemical without deteriorating to an unacceptable extent. Other suitable materials for forming the reservoir are vinyl acetate, vinyl polymers, polyester, polyethylene, polyvinylidene fluoride and nylon, all in fibrous or granular form and formed or moulded with a suitable binding agent or glue.

The reservoir 5 is surrounded by a plastic or acetate film 9, to retain the shape of the reservoir and prevent leakage of the testing chemical. The film 9, like the reservoir 5, must be resistant to the testing chemical so that it does not deteriorate to a great extent in use. Alternatively, the reservoir may be surrounded by a casing such as a glass or plastics tube.

The applicator 7 comprises a nib having a relatively narrow tapered wick 7a at one end, which projects into the reservoir 5 and a wider tip 7b at the other end which projects from the housing through its partly open end 3b. The outer surface of the tip 7b forms an applying surface 8 for applying the testing chemical to an item to be tested. The wick 7a draws up testing chemical from the reservoir 5 and transfers it to the tip. The applicator 7 is dimensioned and shaped to deliver a sufficient quantity of testing chemical to the tip, and thus to the item to be tested, so that a reaction to the chemical is visible to the naked eye.

The applicator 7 is moulded from a fibrous, granular or other porous plastics material that is resistant to the testing chemical. Suitable materials are the same as those used in the reservoir and include polyvinylidene fluoride.

The following table illustrates examples of suitable materials for the applicator and reservoir for different testing chemicals.

| TESTING CHEMICAL | MATERIAL OF RESERVOIR | MATERIAL OF APPLICATOR |
| --- | --- | --- |
| Dilute (e.g.0.5%–20%) sulphuric acid solution containing a silver salt or a chromate | Polypropylene, polyethylene, polyester, nylon, with or without coating | Polypropylene, polyvinylidene fluoride or any material of reservoir |
| Concentrated sulphuric acid containing a silver salt | Polypropylene, polyethylene, polyester, nylon, with or without coating | Polypropylene, polyvinylidene fluoride or any material of reservoir |
| Dilute nitric acid | Polypropylene, polyethylene, polyester, nylon, with or without coating | Polypropylene, polyvinylidene fluoride or any material of reservoir |
| Concentrated nitric acid | Polypropylene, polyethylene, polyester, nylon, with or without coating | Polypropylene, polyvinylidene fluoride or any material of reservoir |
| Nitric acid containing a silver salt or a chromate | Polypropylene, polyethylene, polyester, nylon, with or without coating | Polypropylene, polyvinylidene fluoride or any material of reservoir |
| Hydrochloric acid concentrated or dilute containing stannous chloride | Polypropylene, polyethylene, polyester, nylon, with or without coating | Polypropylene, polyvinylidene fluoride or any material of reservoir |
| Concentrated or dilute Hydrochloric acid | Polypropylene, polyethylene, polyester, nylon, with or without coating | Polypropylene, polyvinylidene fluoride or any material of reservoir |
| Aqua-Regia | Polypropylene, polyvinylidene fluoride both with non-acetate coating and without any acid-dissolvable glues | Polypropylene, polyvinylidene fluoride |

Some of the above mentioned testing chemicals are colorless but some may contain suitable dyes to improve the visibility of the reaction with the item under test.

The apparatus has a cap 11 which covers the tip 7b when the apparatus is not in use. On the closed end 3a of the housing, a "scratcher" 15 is provided for testing jewels. In the embodiment, the scratcher 15 is formed from a small, industrial quality diamond, having a relatively fine point which is used for scratching the surface of the jewel under test. Alternatively, the scratcher 15 may be formed from diamond dust or grit set in a hard wearing glue. The scratcher is used to scratch the surface of the jewel under test and will mark the surface of jewels which are softer than diamond, such as cubic zirconia and other man made simulents.

The scratcher 15 is mounted in a unique way to prevent the user from applying excess pressure to the jewel under test using the scratcher. This ensures that the scratcher does not mark a genuine diamond. The scratcher 15 is thus mounted on an appropriately tensioned spring which limits the amount of pressure that can be applied by the user to the jewel under test. Thus, if the user attempts to apply pressure above a pre-determined level, the spring will be compressed to reduce the pressure of the scratcher on the jewel under test, thus preventing it from being marked. Typically, the scratcher is mounted on a ball or other mounting which is in turn connected to the spring.

It will be appreciated that the scratcher could be made from relatively hard jewels other than diamond, such as sapphire or ruby.

In an alternative embodiment the apparatus could include an electronic diamond tester.

The apparatus in accordance with the invention is quick and easy to use. In addition, since the testing chemical is retained within a sealed reservoir which in turn is housed within a sealed housing, it is readily portable without the risk of leakage and/or breakage. Furthermore, the apparatus automatically applies the appropriate quantity of testing chemical to the item being tested without spillage.

As the skilled person will appreciate, various modifications may be made to the described embodiments. For example, the applicator may be formed of more than one material, for instance, the wick and inner part of the tip may be made from polypropylene and the tip may be covered by a polyvinylidene fluoride layer forming the applying surface. It is intended to include all such variations and modifications as fall within the scope of the accompanying claims.

What is claimed is:

1. An apparatus for testing items of metal comprising; a reservoir containing testing chemical, an applicator for transferring testing chemical from the reservoir to an applying surface thereof, a housing surrounding the reservoir and applicator with the applying surface projecting therefrom, and in which the testing chemical comprises an acid selected from the group consisting of sulphuric acid, nitric acid and hydrochloric acid and a chemical selected from the group consisting of a silver salt, a chromate and a dichromate.

2. Apparatus as claimed in claim 1, wherein the reservoir is surrounded by a material which is resistant to deterioration by the testing chemical.

3. Apparatus as claimed in claim 1, wherein the applicator comprises a nib having a wick in contact with testing chemical within the reservoir.

4. Apparatus as claimed in claim 3, wherein the nib is formed of a material which is resistant to deterioration by the testing chemical.

5. Apparatus as claimed in claim 4, wherein the nib is formed from a material selected form the group consisting of polyethylene, polypropylene and polyvinylidene fluoride.

6. Apparatus as claimed in claim 1, further comprising a hard jewel carried by the housing, the jewel being selected from the group consisting of diamonds, rubies and sapphires.

7. Apparatus as claimed in claim 6, including means for resiliently mounting the hard jewel to the housing.

8. Apparatus as claimed in claim 7, in which the hard jewel is diamond grit which is mounted indirectly on a spring.

9. Apparatus as claimed in claim 1, wherein the reservoir comprises a porous plastic material.

10. Apparatus for testing items of metal comprising; a reservoir containing a testing chemical, an applicator for transferring the testing chemical from the reservoir to an applying surface thereof, a housing surrounding the reservoir and applicator with the applying surface projecting therefrom, and a hard jewel carried by the housing and selected from the group consisting of diamonds, sapphires and rubies.

11. Apparatus for testing items of metal comprising: a reservoir containing testing chemical; an applicator for transferring testing chemical from the reservoir to an applying surface thereof, a housing surrounding the reservoir and applicator with the applying surface projecting therefrom, and in which the testing chemical comprises stannous chloride and hydrochloric acid.

12. Apparatus as claimed in claim 11, wherein the reservoir is surrounded by a material which is resistant to deterioration by the testing chemical.

13. Apparatus as claimed in claim 11, wherein the applicator comprises a nib having a wick in contact with testing chemical within the reservoir.

14. Apparatus as claimed in claim 13, wherein the nib is formed of a material which is resistant to deterioration by the testing chemical.

15. Apparatus as claimed in claim 14, wherein the nib is formed from a material selected form the group consisting of: polyethylene, polypropylene and polyvinylidene.

16. Apparatus as claimed in claim 11, wherein the reservoir comprises a porous plastic material.

* * * * *